United States Patent
Mendez et al.

[11] 3,953,301
[45] Apr. 27, 1976

[54] RECOVERY OF HEXANE FROM RECYCLE STREAMS FROM ETHYLENE POLYMERIZATION REACTORS

[75] Inventors: Tomas Mendez, Orange; Guy Van Cleve, Jr., Port Arthur, both of Tex.

[73] Assignee: Gulf Oil Corporation, Pittsburgh, Pa.

[22] Filed: Sept. 5, 1974

[21] Appl. No.: 503,525

[52] U.S. Cl. .................................. 203/75; 203/94; 526/68; 526/70; 526/330; 526/352
[51] Int. Cl.² ...................... B01D 3/00; B01D 3/10
[58] Field of Search .................. 203/71, 73, 74, 75, 203/78, 81, 82, 84, 91, 94, 98, DIG. 10, DIG. 21, 68, 70, 60; 260/94.9 F, 499

[56] References Cited
UNITED STATES PATENTS

| | | | |
|---|---|---|---|
| 3,182,006 | 5/1965 | Fruhwirth | 203/68 |
| 3,277,158 | 10/1966 | Schaffer | 260/499 |
| 3,324,090 | 6/1967 | Ross et al. | 260/94.9 F |
| 3,394,057 | 7/1968 | Miller et al. | 203/DIG. 10 |

*Primary Examiner*—Frank W. Lutter
*Assistant Examiner*—Frank Sever

[57] ABSTRACT

A process is provided for recovering hexane from the mixed recycle stream from a plurality of ethylene polymerization reactors. The recycle stream containing hexane and periodically vinyl acetate and/or an alkyl acrylate admixed with vinyl acetate to provide a mixed feed stream containing at least 45% by weight vinyl acetate. This feed stream is distilled at atmospheric pressure and all of the hexane is recovered as an overhead azeotrope containing about 57% hexane. The overhead fraction is redistilled at a superatmospheric pressure of at least 4 atmospheres in a second column. The overhead fraction of the second column will be enriched in vinyl acetate and pure hexane is recovered as a bottoms fraction from the second column. The vinyl acetate and/or alkyl acrylate contained in the bottoms fraction of the first column is recovered by atmospheric distillation in a third column.

4 Claims, 1 Drawing Figure

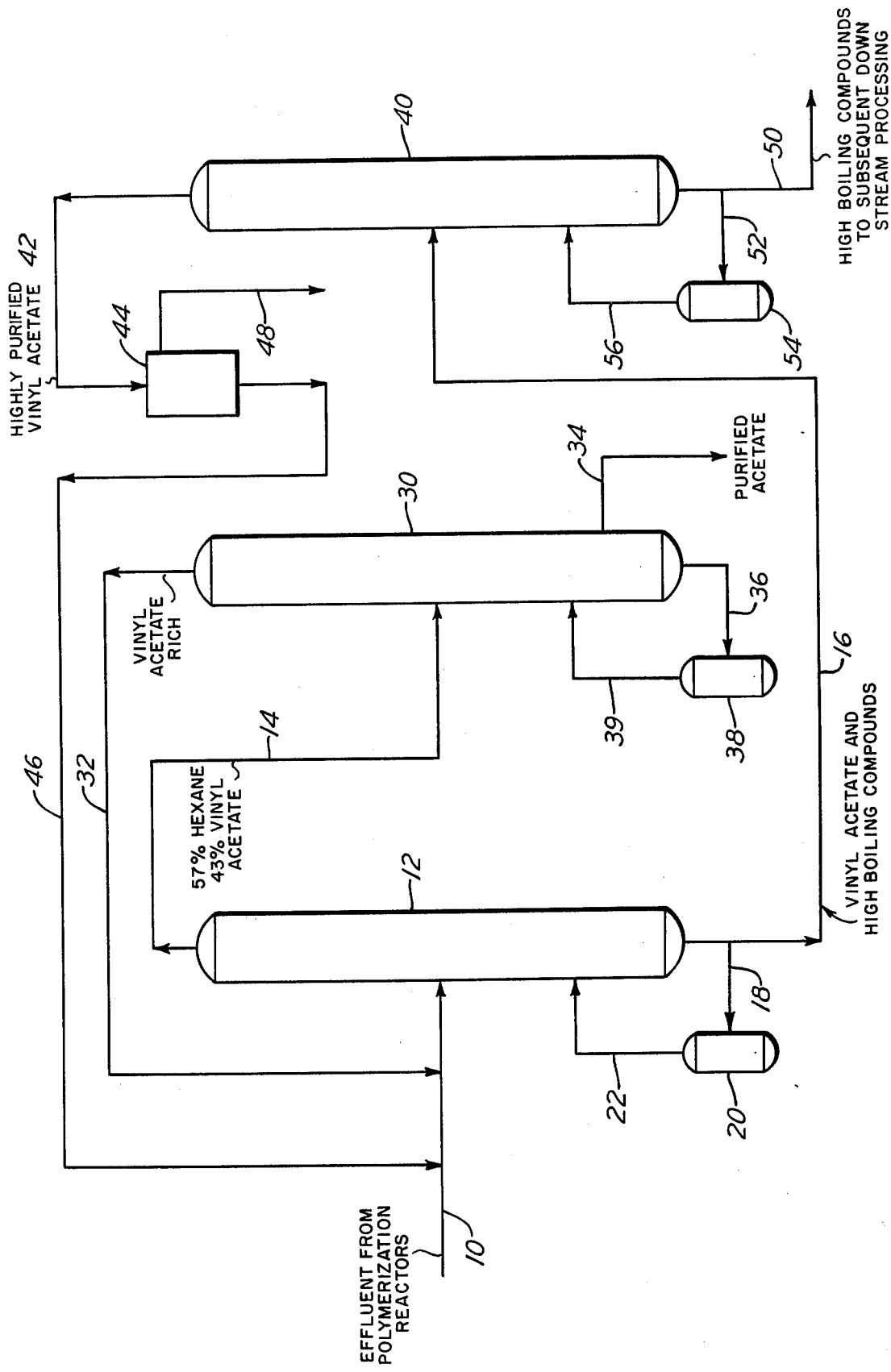

3,953,301

RECOVERY OF HEXANE FROM RECYCLE STREAMS FROM ETHYLENE POLYMERIZATION REACTORS

BACKGROUND OF THE INVENTION

In a high pressure polymerization of ethylene, hexane is commonly employed as a solvent or carrier for catalysts and other minor components fed to the polymerization reactor. Hexane is used for this purpose not only in the homopolymerization of ethylene, but also in the copolymerization of ethylene with other monomers such as vinyl acetate and alkyl acrylates.

The hexane employed for this purpose is of a highly purified grade so that it contains no components having an adverse effect upon the polymerization. For this reason, the hexane contained in the discharge or recycle stream from the polymerization reactor is recovered for reuse. The recovery of such hexane normally is not difficult, when the ethylene polymerization plant is employed solely to prepare ethylene homopolymers.

In a typical ethylene polymerization plant, several polymerization reactors are provided and the discharge or recycle streams of the several reactors usually are combined for purification and recycling. The combined discharge stream for recycling will contain unpolymerized comonomers such as vinyl acetate and alkyl acrylates, when copolymers of such monomers are being produced in one or more of the polymerization reactors. Very substantial difficulties are encountered in recovering hexane from such combined discharge streams by reason of the fact that hexane forms azeotropes with both vinyl acetate and alkyl acrylates. It is, of course, essential to recover the hexane in a highly purified form if it subsequently is to be employed as a carrier for components to be employed in the homopolymerization of ethylene. The problem of recovering purified hexane and the concomitant problem of avoiding the introduction of vinyl acetate and/or alkyl acrylates in the intended homopolymerization of ethylene is of such magnitude that frequently operators of ethylene polymerization plants will burn such combined discharge streams as fuel in lieu of recovering the hexane therefrom.

SUMMARY OF THE INVENTION

In accordance with the present invention, a process involving the use of three distillation columns is employed so that purified hexane can be continuously recovered from the combined discharge or recycle streams from a plurality of ethylene polymerization reactors, regardless of whether said recycle stream contains only hexane or also varying quantities of vinyl acetate and/or alkyl acrylates. The process involves feeding such a recycle stream to a first distillation column together with one or both overhead fractions from the other two distillation columns, both of which overhead fractions contain vinyl acetate. The combined feed to the first polymerization reactor is adjusted so that the feed to the first column contains at least about 45% by weight of vinyl acetate.

In the first distillation column, the distillation is run at atmospheric pressure and all of the hexane fed to the distillation column is removed as an overhead fraction. This overhead fraction is a binary azeotrope of hexane and vinyl acetate, which contains substantially 43% vinyl acetate. The overhead stream from the first distillation column is fed to a second distillation column which is operated at a superatmospheric pressure of at least 4 atmospheres. All of the vinyl acetate fed to the second column is removed as an overhead fraction. This overhead fraction is a binary azeotrope of hexane and vinyl acetate which contains in excess of 43% by weight of vinyl acetate. All of the overhead fraction from the second distillation column is recycled as feed to the first distillation column. The bottoms fraction from the second distillation column consists of purified hexane which is recovered for subsequent reuse.

The bottoms fraction from the first distillation column is fed to a third distillation column which is operated at atmospheric pressure. All of the vinyl acetate fed to the third column is recovered as a purified overhead fraction. The overhead fraction of vinyl acetate is recycled as needed to the first distillation column to maintain the vinyl acetate level in the feed to the first distillation column at a level of at least 45% by weight vinyl acetate. Any vinyl acetate in excess of this requirement is recovered for reuse.

The bottoms fraction from the third distillation column contains any alkyl acrylate contained in the recycle stream fed to the first distillation column plus any other high boiling organic compound contained in such recycle stream.

DESCRIPTION OF THE DRAWING

FIG. 1 is a flow sheet of the process of the invention.

DETAILED DESCRIPTION OF THE INVENTION

In the drawing, a recycle stream from a plurality of ethylene polymerization reactors is fed through line 10 to a first distillation column 12. The recycle stream fed through line 10 is made up of nonpolymerized compounds recovered from a pluarlity of ethylene polymerization reactors and has been previously passed through one or more columns to remove therefrom unpolymerized ethylene and any other compounds boiling below 69°C. The overhead fractions from the second and third distillation columns are fed into line 10 through lines 32 and 46. The relative rates of flow through lines 32 and 46 are adjusted by valve means not shown so that the composition of the material fed to distillation column 12 contains at least 45% by weight of vinyl acetate. The balance of the material fed to distillation column 12 will consist principally of hexane plus any alkyl acrylate and/or other high boiling organic compounds included in the recycle stream from the ethylene polymerization reactors.

Distillation column 12 is operated at atmospheric pressure and all of the hexane fed to the distillation column 12 is removed as an overhead fraction through line 14. This overhead fraction will contain substantially 57% hexane and 43% vinyl acetate.

The overhead fraction from line 14 is fed to a second distillation column 30 which is operated at a superatmospheric pressure of at least 4 atmospheres. Under superatmospheric pressure, the composition of the minimum boiling azeotrope formed between hexane and vinyl acetate changes and is enriched in vinyl acetate. At a pressure of 6 atmospheres, the binary azeotrope contains 50% hexane and 50% vinyl acetate. All of the vinyl acetate fed to distillation column 30 is thus removed as an overhead fraction through line 32 and is fed into line 10 for recycling to the first distillation column 12.

The bottoms fraction in distillation column 30 consists of purified hexane which is recovered through line 34. A small portion of bottoms fraction is removed through line 36, is fed to a reboiler 38, and subsequently is reintroduced into distillation column 30 through line 39.

The bottoms fraction from distillation column 12 consists of vinyl acetate and other high boiling compounds including any alkyl acrylate introduced into distillation column 12. This bottoms fraction is removed from the column through line 16. A portion of the bottoms fraction is removed from line 16 through line 18, is fed to a reboiler 20, and subsequently is reintroduced into distillation column 12 through line 22.

The bottoms fraction from distillation column 12 is fed through line 16 into a third distillation column 40. Distillation column 40 is operated at substantially atmospheric pressure and highly purified vinyl acetate is recovered as an overhead fraction through line 42. The vinyl acetate from line 42 is collected in a storage tank 44. Vinyl acetate is removed from tank 44 and recycled through line 46 to line 10 as needed to maintain a minimum concentration of 45% by weight of vinyl acetate in the material fed into first distillation column 12. As storage tank 44 fills with vinyl acetate, a portion thereof is recovered through line 48.

The bottoms fraction from distillation column 40 will consist of any alkyl acrylate included in the recycle stream introduced into the system through line 10 plus any other compounds in such recycle stream which have an atmospheric boiling point above 72°C. Such high boiling components, when present, are the decomposition products of the catalysts fed to the polymerization reactors, or certain telogenating agents fed to the polymerization reactors, or low molecular weight polymers of ethylene. The bottoms fraction from distillation column 40 is removed through line 50 for subsequent downstream processing not shown. A portion of the bottoms fraction from line 50 is removed through line 52, is fed to a reboiler 54, and subsequently is reintroduced into column 40 through line 56.

In a typical mode of operation, a recycle stream from a plurality of ethylene polymerization reactors will be fed through line 10 into distillation column 12 at a rate of 1880 lbs. per hour. Such recycle stream will have a typical composition consisting of 53.2% hexane, 26.3% vinyl acetate and 10.8% methyl acrylate, and 9.7% of higher boiling components. The overhead fraction from distillation column 30 will be introduced into line 10 through line 32 at a rate of 8,020 lbs. per hour. The material recycled through line 32 will contain 50 weight % hexane and 50 weight % vinyl acetate. The pure vinyl acetate overhead from distillation column 40 will be introduced into line 10 through line 46 at a rate of 100 lbs. per hour. Hexane will be recovered as a bottoms fraction from distillation column 30 at a rate of 990 lbs. per hour. Purified vinyl acetate will be recovered for reuse through line 48 at a rate of 265 lbs. per hour.

A significant advantage of the invention is its ability to continuously recover hexane from recycle streams containing widely varying concentrations of vinyl acetate and/or alkyl acrylates. When the recycle stream contains relatively large concentrations of vinyl acetate, substantial quantities of vinyl acetate will be recovered through line 48. When the recycle stream contains little or no vinyl acetate, all of the vinyl acetate contained in the system is used as recycle. Thus, the process of the invention has the capability of accepting and handling large fluctuations in contraction of vinyl acetate and/or alkyl acrylates without disturbing the quality of the hexane being recovered through line 34.

The process of the invention may be used with the commercial grades of n-hexane sold for use as catalyst carriers in the polymerization of ethylene. Such commercial hexanes normally will contain about 90 mol % n-hexane, about 7 mol % methyl cyclopentane, about 3 mol % 3-methylpentane and traces of other hexane isomers. In the operation of the process, it is desirable to avoid adding to the polymerization reactors any compounds which will form a ternary azeotrope with hexane and vinyl acetate or a binary azeotrope with vinyl acetate.

What is claimed is:

1. A method for continuously recovering hexane from the mixed recycle stream from a plurality of ethylene polymerization reactors, said recycle stream always containing hexane and periodically containing at least one chemical from the group consisting of vinyl acetate, alkyl acrylate esters, and other organic chemicals, which have an atmospheric boiling point higher than 72°C. and which do not form a ternary azeotrope with hexane and vinyl acetate and which do not form a binary azeotrope with vinyl acetate, which method consists essentially of:
  1. Feeding to a first distillation column, a distillable mixture containing hexane and at least 45 wt% vinyl acetate, said distillable mixture being formed by combining,
     a. A recycle stream from a plurality of ethylene polymerization reactors, which recycle stream contains hexane,
     b. The total overhead fraction from step 7, and
     c. At least a portion of the overhead fraction of step 12; said portion being used to maintain said at least 45 wt% vinyl acetate in the distillable mixture
  2. operating said first distillation column at atmospheric pressure;
  3. recovering from said first distillation column an overhead fraction containing substantially 57% by weight of hexane and 43% by weight of vinyl acetate;
  4. recovering from said first distillation column a bottoms fraction free of hexane and containing only vinyl acetate and compounds other than hexane and vinyl acetate included in the recycle stream fed to step (1);
  5. feeding the overhead fraction from step (3) to a second distillation column;
  6. operating said second distillation column at a pressure of at least 4 atmospheres;
  7. recovering from said second distillation column an overhead fraction containing in excess of 43% by weight of vinyl acetate and the balance hexane;
  8. recovering from said second distillation column a bottoms fraction consisting entirely of hexane;
  9. recycling the entire overhead fraction from step (7) to step (1);
  10. feeding the bottoms fraction from step (4) to a third distillation column;
  11. operating said third distillation column at substantially atmospheric pressure;
  12. recovering from said third distillation column an overhead fraction consisting solely of vinyl acetate;

13. recovering from said third distillation column a bottoms fraction consisting solely of the chemicals other than hexane and vinyl acetate included in the recycle stream fed to step (1); and
14. recycling at least a portion of the overhead fraction from step (12) to step (1) to maintain the concentration of vinyl acetate in step (1) at a level of at least 45% by weight of the material fed to the first distillation column.

2. The method of claim 1 in which the recycle stream consists principally of a mixture of hexane and vinyl acetate.

3. The method of claim 1 in which the recycle stream consists principally of a mixture of hexane and an alkyl acrylate.

4. The method of claim 1 in which the recycle stream consists principally of a mixture of hexane, vinyl acetate and an alkyl acrylate.

* * * * *

UNITED STATES PATENT AND TRADEMARK OFFICE
CERTIFICATE OF CORRECTION

PATENT NO. : 3,953,301
DATED : April 27, 1976
INVENTOR(S) : Tomas Mendez and Guy Van Cleve, Jr.

It is certified that error appears in the above-identified patent and that said Letters Patent are hereby corrected as shown below:

Column 2, line 35 "pluarlity" should read --- plurality ---.

In the drawing, the legend at the bottom of line 34 should read "PURIFIED HEXANE."

Signed and Sealed this

Fourteenth Day of September 1976

[SEAL]

Attest:

RUTH C. MASON
*Attesting Officer*

C. MARSHALL DANN
*Commissioner of Patents and Trademarks*